US012654170B2

(12) United States Patent
Wang et al.

(10) Patent No.: US 12,654,170 B2
(45) Date of Patent: Jun. 16, 2026

(54) HOLE ARRAY LAYERED STRUCTURE, PRECOATING METHOD, MEMBRANE FORMING METHOD AND SEQUENCING DEVICE

(71) Applicant: Qitan Technology Ltd., Chengdu, Chengdu (CN)

(72) Inventors: Jin Wang, Chengdu (CN); Mingzhao Guo, Chengdu (CN); Wei Zhai, Chengdu (CN); Youna Zhang, Chengdu (CN)

(73) Assignee: Qitan Technology Ltd., Chengdu, Chengdu (CN)

( * ) Notice: Subject to any disclaimer, the term of this patent is extended or adjusted under 35 U.S.C. 154(b) by 252 days.

(21) Appl. No.: 18/204,573

(22) Filed: Jun. 1, 2023

(65) Prior Publication Data
US 2023/0398544 A1     Dec. 14, 2023

Related U.S. Application Data

(63) Continuation of application No. PCT/CN2022/098558, filed on Jun. 14, 2022.

(51) Int. Cl.
*B01L 3/00*        (2006.01)
*G01N 27/447*     (2006.01)
*G01N 33/487*     (2006.01)

(52) U.S. Cl.
CPC ...... *B01L 3/5085* (2013.01); *G01N 27/44791* (2013.01); *G01N 33/48721* (2013.01);
(Continued)

(58) Field of Classification Search
CPC ............... B01L 3/5085; B01L 3/50857; B01L 2200/12; B01L 2300/0819;
(Continued)

(56) References Cited

U.S. PATENT DOCUMENTS

| | | | |
|---|---|---|---|
| 2002/0179448 A1 | 12/2002 | Lauks | |
| 2015/0014160 A1* | 1/2015 | Hyde | ............... G01N 27/44791 |
| | | | 204/403.01 |

(Continued)

FOREIGN PATENT DOCUMENTS

| | | |
|---|---|---|
| CN | 104918696 A | 9/2015 |
| CN | 104918696 B | 11/2018 |

(Continued)

OTHER PUBLICATIONS

Notification of Grant dated Aug. 23, 2022 issued for Chinese Patent Application No. 202210664631.8.

(Continued)

*Primary Examiner* — Shizhi Qian
(74) *Attorney, Agent, or Firm* — K&L Gates LLP

(57)        ABSTRACT
Embodiments of the present application provide a hole array layered structure, a precoating method, a membrane forming method and a sequencing device. The hole array layered structure is adapted for forming a membrane forming space with a substrate, wherein the membrane forming space is adapted to form a membrane layer. The hole array layered structure includes a base plate, a plurality of hole units is provided in the base plate in an array, each hole unit penetrates through the base plate and includes a first hole and a second hole stacked in a thickness direction of the base plate, a first hole contour of the first hole surrounds a second hole contour of the second hole on an outer side thereof, the (Continued)

second holes of the plurality of hole units are disconnected with each other, and the first holes of the plurality of hole units are disconnected with each other.

21 Claims, 19 Drawing Sheets

(52) U.S. Cl.
CPC ... *B01L 2200/12* (2013.01); *B01L 2300/0819* (2013.01); *B01L 2300/0829* (2013.01)

(58) Field of Classification Search
CPC ...... B01L 2300/0829; G01N 27/44791; G01N 33/48721
See application file for complete search history.

(56) References Cited

U.S. PATENT DOCUMENTS

| | | | |
|---|---|---|---|
| 2015/0265994 A1 | 9/2015 | Hyde et al. | |
| 2016/0361717 A1 | 12/2016 | Wilson et al. | |
| 2022/0396013 A1* | 12/2022 | Ortiz Bahamon | ........................... G01N 33/48721 |
| 2023/0092634 A1* | 3/2023 | Li | ..................... G01N 33/48721 204/451 |
| 2023/0228732 A1* | 7/2023 | Xie | ................... G01N 33/48721 422/68.1 |
| 2024/0375107 A1* | 11/2024 | Yun | ........................ B01L 3/5085 |
| 2025/0067703 A1* | 2/2025 | Zhang | .................. C12Q 1/6869 |

FOREIGN PATENT DOCUMENTS

| | | |
|---|---|---|
| CN | 109569458 A | 4/2019 |
| CN | 113070113 A | 7/2021 |
| CN | 113426499 A | 9/2021 |
| CN | 216208593 U | 4/2022 |
| CN | 216337555 A | 4/2022 |
| CN | 114460135 A | 5/2022 |
| KR | 20030018698 A | 3/2003 |
| WO | WO2021078971 A2 | 4/2021 |

OTHER PUBLICATIONS

First Office Action dated Jul. 25, 2022 issued for Chinese Patent Application No. 202210664631.8.
International Search Report dated Mar. 6, 2023 issued for International PCT Application No. PCT/CN2022/098558.

* cited by examiner

13

112          112

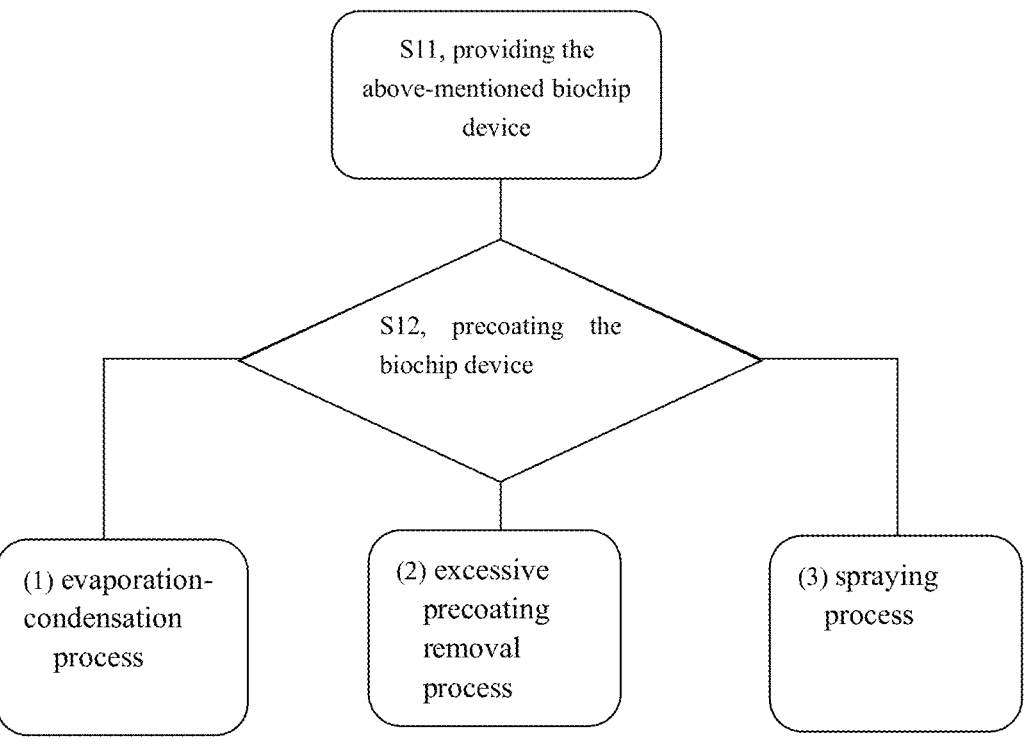

Fig. 23

S1211, orienting openings of the hole units in the biochip device towards an evaporation position S1212, providing a precoating means which contains a precoating material, placing the precoating means at the evaporation position with an opening of the precoating means facing the biochip device, heating the precoating means to an evaporation threshold, and stopping the precoating after heating for a predetermined time

Fig. 24

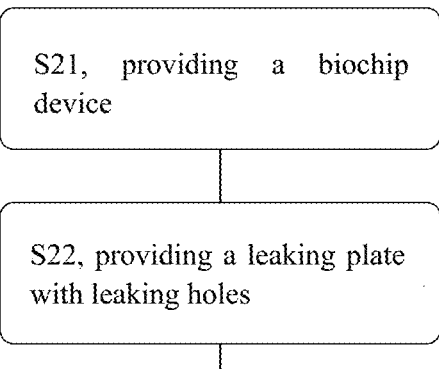

S21, providing a biochip device

S22, providing a leaking plate with leaking holes

S23, providing a scraping means so that an edge of the scraping means is attached to a side of the leaking plate facing away from the biochip device and the scraping means is movable relative to the leaking plate S24, taking a precoating material and placing it on one side of the leaking plate, moving the scraping means so as to push the precoating material to move towards the other side of the leaking plate, when a movement track of the precoating material passes across respective leaking holes, the precoating material enters the hole units through the leaking holes

Fig. 29

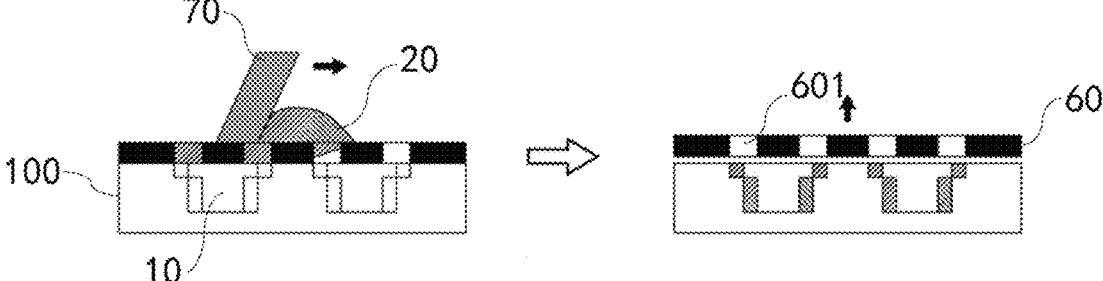

Fig. 30

S31, providing a biochip device

S32, providing a printing plate provided with a transfer portion, such as any surface of the printing plate, and movable relative to the biochip device, when the printing plate covers the biochip device on a side of openings of the hole units, a portion of the printing plate attached to the biochip device is located within the transfer portion S33, taking a precoating material and uniformly disposing the precoating material on the transfer portion S34, performing a transfer printing: covering the biochip device on the side of the openings of the hole units by the printing plate provided with the precoating material on its transfer portion, transferring the precoating material from the transfer portion of the printing plate into the hole units of the biochip device, and maintaining the covering state until the precoating material in the hole units reaches a precoating threshold

Fig. 31

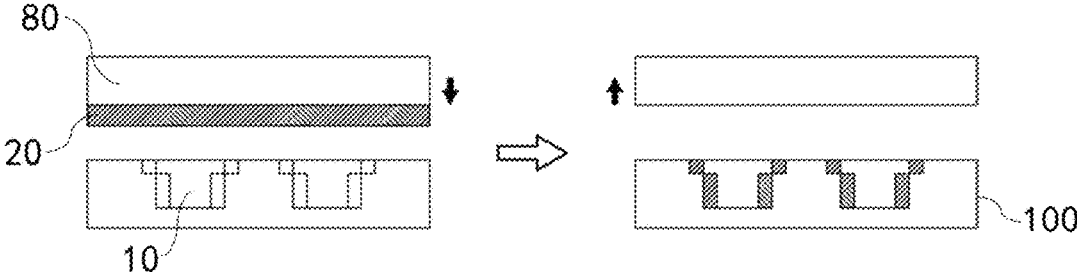

Fig. 32

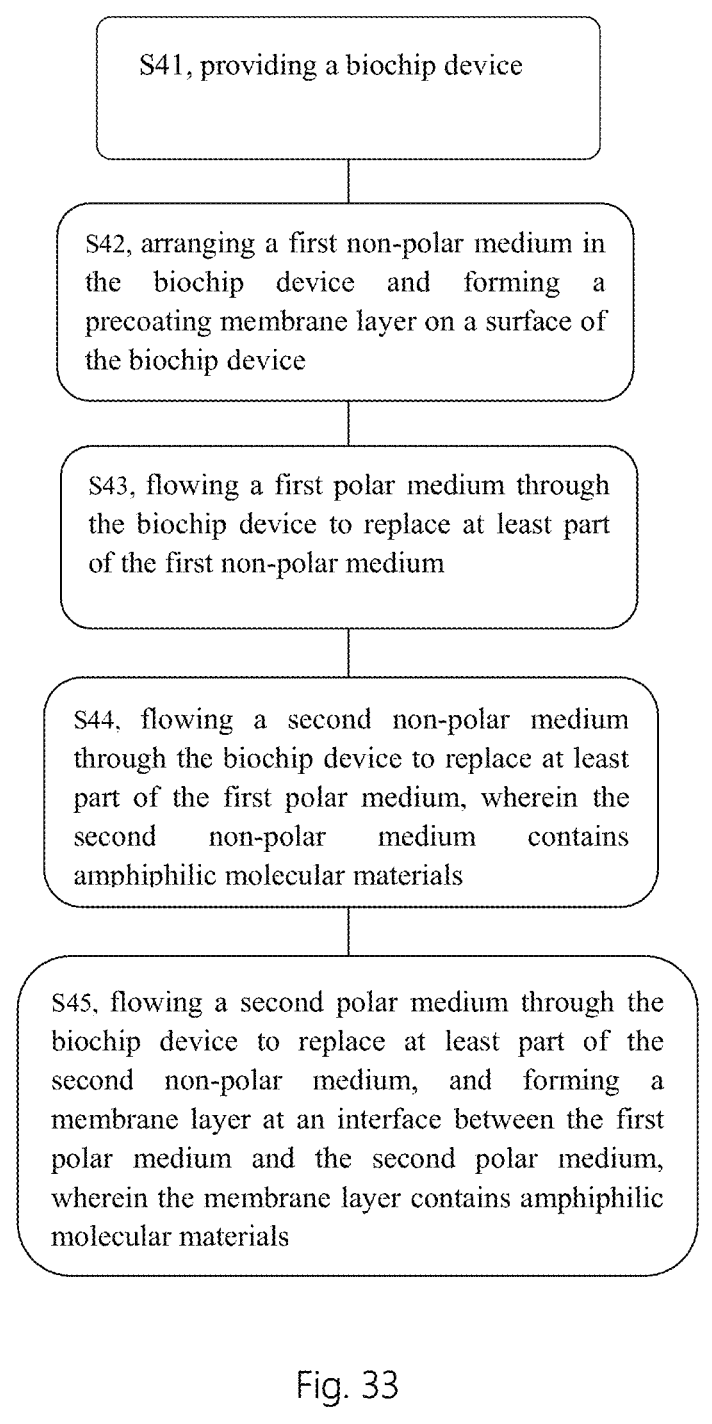

S41, providing a biochip device

S42, arranging a first non-polar medium in the biochip device and forming a precoating membrane layer on a surface of the biochip device S43, flowing a first polar medium through the biochip device to replace at least part of the first non-polar medium S44, flowing a second non-polar medium through the biochip device to replace at least part of the first polar medium, wherein the second non-polar medium contains amphiphilic molecular materials S45, flowing a second polar medium through the biochip device to replace at least part of the second non-polar medium, and forming a membrane layer at an interface between the first polar medium and the second polar medium, wherein the membrane layer contains amphiphilic molecular materials

Fig. 33

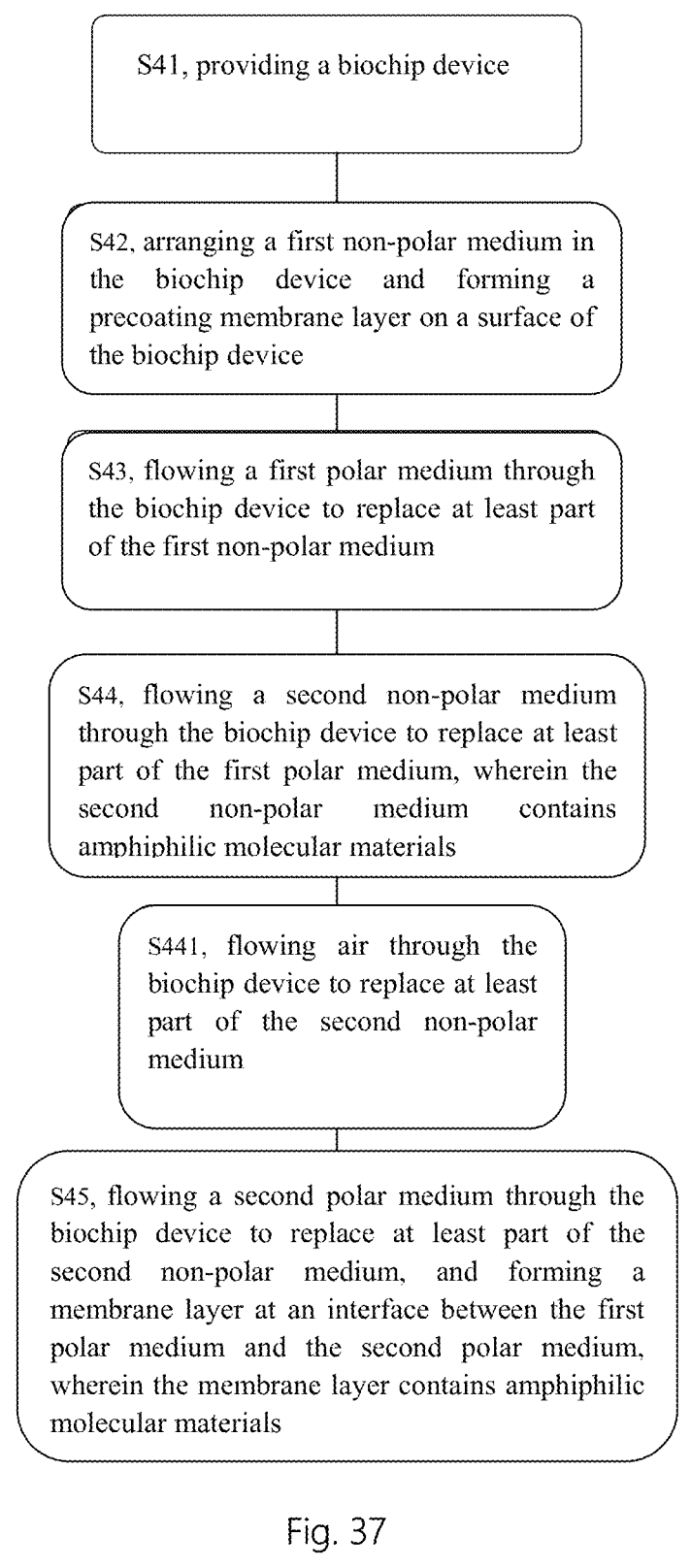

S41, providing a biochip device

S42, arranging a first non-polar medium in the biochip device and forming a precoating membrane layer on a surface of the biochip device S43, flowing a first polar medium through the biochip device to replace at least part of the first non-polar medium S44, flowing a second non-polar medium through the biochip device to replace at least part of the first polar medium, wherein the second non-polar medium contains amphiphilic molecular materials S441, flowing air through the biochip device to replace at least part of the second non-polar medium S45, flowing a second polar medium through the biochip device to replace at least part of the second non-polar medium, and forming a membrane layer at an interface between the first polar medium and the second polar medium, wherein the membrane layer contains amphiphilic molecular materials

Fig. 37

HOLE ARRAY LAYERED STRUCTURE, PRECOATING METHOD, MEMBRANE FORMING METHOD AND SEQUENCING DEVICE

CROSS REFERENCES TO RELATED APPLICATIONS

The present application is a continuation of PCT Application No. PCT/CN2022/098558, filed on Jun. 14, 2022 and entitled by "Hole Array Layered Structure, Precoating Method, Membrane Forming Method and Sequencing Device", which is incorporated herein by reference.

TECHNICAL FIELD

The present application belongs to the field of biological detection technology, in particular to a hole array layered structure, a precoating method, a membrane forming method and a sequencing device.

BACKGROUND

In nanopore sequencing, analytes such as biomacromolecules are driven to pass through nanopore sequencing channels embedded in support membranes (such as lipid membranes) by applying a certain electric potential, and the biomacromolecules passing through the nanopore sequencing channels are identified by current changes caused by different chemical groups passing through the nanopore sequencing channels. The structure that forms the nanopores is usually divided into two layers, and the structures in the upper layer are connected with each other, but after the membrane forming process, the interconnection structures of the upper layer tend to cause mediums to flow in the respective nanopores, which seriously affects the stability after the membrane formation.

SUMMARY

The embodiments of the present application provide a hole array layered structure, a precoating method, a membrane forming method and a sequencing device to solve the problem of instability after the membrane forming process in the prior art.

A first aspect of the embodiments of the present application provide a hole array layered structure for forming a membrane forming space with a substrate, wherein the membrane forming space is adapted to form a membrane layer, and the hole array layered structure includes: a base plate; and a plurality of hole units provided in the base plate and arranged in an array, each hole unit penetrating through the base plate and comprising a first hole and a second hole stacked in a thickness direction of the base plate, the second hole being configured to be connected with the substrate, a projection of the first hole on a plane perpendicular to the thickness direction of the base plate having a first hole contour, a projection of the second hole on the plane perpendicular to the thickness direction of the base plate having a second hole contour, and the first hole contour surrounding the second hole contour on an outer side thereof, the second holes of the plurality of hole units are disconnected with each other to prevent mediums in the respective second holes from flowing among a plurality of second holes, and the first holes of the plurality of hole units are disconnected with each other to prevent mediums in the respective first holes from flowing among a plurality of first holes.

With the above structure, the side wall of the first hole is provided to be closed, which can make the respective hole units relatively independent and reduce movement of the mediums among the respective hole units after the membrane formation, especially when the membrane in the hole unit breaks, the polar solvent below the membrane in the hole unit diffuses into other hole units along the first hole and further affecting the stability of other hole units.

In some optional implementations of the present application, the hole array layered structure further includes first tooth slots extending outward from a side wall of the first hole perpendicularly to the thickness direction of the base plate, a plurality of first tooth slots are provided in a circumferential direction of the first hole, and each of the first tooth slots has an opening communicated with the first hole at the first hole contour, and in a projection on the plane perpendicular to the thickness direction of the base plate, extension lengths from slot bottoms to openings of the respective first tooth slots are different.

In some optional implementations of the present application, on the plane perpendicular to the thickness direction of the base plate, a contour constrained by projections of the slot bottoms of the plurality of first tooth slots and extension lines thereof is defined as a first tooth slot outer contour, and the first tooth slot outer contour is in a shape of a regular polygon or a circle.

In some optional implementations of the present application, on the plane perpendicular to the thickness direction of the base plate, axes of the plurality of first tooth slots extend and intersect at a center of the first tooth slot outer contour.

In some optional implementations of the present application, the hole array layered structure further includes second tooth slots extending outward from a side wall of the second hole perpendicularly to the thickness direction of the base plate, a plurality of second tooth slots are provided in a circumferential direction of the second hole, and each of the second tooth slots has an opening communicated with the second hole at the second hole contour.

In some optional implementations of the present application, on the plane perpendicular to the thickness direction of the base plate, a contour constrained by projections of the openings of the plurality of first tooth slots and extension lines thereof is the first hole contour, a contour constrained by projections of slot bottoms of the plurality of second tooth slots and extension lines thereof is defined as a second tooth slot outer contour, and the second tooth slot outer contour is consistent with the first hole contour.

In some optional implementations of the present application, the first tooth slot outer contour is in a shape of a regular polygon, and the first hole contour is in a shape of a circle.

In some optional implementations of the present application, the first tooth slot outer contour is in a shape of a circle, and the first hole contour is in a non-circular shape.

In some optional implementations of the present application, on the plane perpendicular to the thickness direction of the base plate, a contour constrained by projections of openings of the second tooth slots and extension lines thereof is the second hole contour, the second hole contour is located within the first hole contour, and the second hole contour is in a shape of a circle, the center of the first tooth slot outer contour coincides with a center of the second hole contour.

In some optional implementations of the present application, on the plane perpendicular to the thickness direction of the base plate, axes of the plurality of second tooth slots extend and intersect at the center of the second hole contour.

In some optional implementations of the present application, the base plate is provided with a plurality of hole units, channels are further provided between adjacent hole units, the channels extend in the thickness direction of the base plate, and on the plane perpendicular to the thickness direction of the base plate, projections of the channels are consistent with projections of the first tooth slot outer contours.

In some optional implementations of the present application, in the hole array layered structure, the first tooth slots of one of the plurality of hole units are aligned with the first tooth slots of adjacent hole units.

In some optional implementations of the present application, in the hole array layered structure, the first tooth slots of one of the plurality of hole units are staggered with the first tooth slots of adjacent hole units.

In some optional implementations of the present application, side walls of the channels are provided with a plurality of third tooth slots extending outward perpendicularly to the thickness direction of the base plate.

In some optional implementations of the present application, on the plane perpendicular to the thickness direction of the base plate, axes of the plurality of third tooth slots extend and intersect at the center of the first tooth slot outer contour.

A second aspect of the embodiments of the present application provide a biochip device, including: a substrate; and the hole array layered structure as described above. The hole array layered structure is located on the substrate, and the first holes of the hole units are located on a side of the second holes of the hole units facing away from the substrate.

A third aspect of the embodiments of the present application provide a precoating method for a biochip device, the method including the following steps:

providing the biochip device as described above;

precoating the biochip device, wherein the precoating includes any of the following processes:

(1) an evaporation-condensation process, including: orienting openings of the hole units in the biochip device towards an evaporation position; providing a precoating means which contains a precoating material and placing the precoating means at the evaporation position with an opening of the precoating means facing the biochip device, heating the precoating means to an evaporation threshold, and stopping the precoating after heating for a predetermined time;

(2) an excessive precoating removal process, including: adding a precoating material greater than a precoating threshold to the hole units, and removing the precoating material in the hole units to the precoating threshold; and (3) a spraying process, including: taking the biochip device and a printer, disposing a precoating material in the printer, aligning printing heads of the printer with edges of the hole units on the biochip device, starting the printer, and spraying a predetermined amount of the precoating material into the hole units.

In some optional implementations of the present application, the step of removing the precoating material in the hole units to the precoating threshold further includes: heating the biochip device to evaporate the precoating material until the precoating material in the hole units reaches the precoating threshold.

In some optional implementations of the present application, the step of removing the precoating material in the hole units to the precoating threshold further includes: providing a suction means and covering the base plate on a side of the openings of the hole units by the suction means until the precoating material in the hole units reaches the precoating threshold.

In some optional implementations of the present application, a precoating method for a biochip device is further provided, the method including the following steps:

providing the biochip device as described above;

providing a leaking plate with leaking holes, and covering the biochip device on a side of openings of the hole units by the leaking plate so that edges of the hole units correspond to at least one leaking hole on the leaking plate;

providing a scraping means so that an edge of the scraping means is attached to a side of the leaking plate facing away from the biochip device and the scraping means is movable relative to the leaking plate; and taking a precoating material and placing it at the scraping means, moving the scraping means to push the precoating material to move on the leaking plate, wherein when a movement track of the precoating material passes across respective leaking holes, the precoating material enters the hole units through the leaking holes.

In some optional implementations of the present application, a precoating method for a biochip device is further provided, the method including the following steps:

providing the biochip device as described above;

providing a printing plate which is provided with a transfer portion, wherein when the printing plate covers the biochip device on a side of openings of the hole units, a portion of the printing plate attached to the biochip device is located within the transfer portion;

taking a precoating material and uniformly disposing the precoating material on the transfer portion; and performing a transfer printing: covering the biochip device on the side of the openings of the hole units by the printing plate provided with the precoating material on its transfer portion, transferring the precoating material from the transfer portion of the printing plate into the hole units of the biochip device, and maintaining the covering state until the precoating material in the hole units reaches a precoating threshold and then stopping the precoating.

A fourth aspect of embodiments of the present application provide a membrane forming method, the method including the following steps of:

providing the biochip device as described above;

arranging a first non-polar medium in the biochip device and forming a precoating membrane layer on a surface of the biochip device;

flowing a first polar medium through the biochip device to replace at least part of the first non-polar medium;

flowing a second non-polar medium through the biochip device to replace at least part of the first polar medium, wherein the second non-polar medium contains amphiphilic molecular materials; and flowing a second polar medium through the biochip device to replace at least part of the second non-polar medium, and forming a membrane layer at an interface between the first polar medium and the second polar medium, wherein the membrane layer contains amphiphilic molecular materials.

In some optional implementations of the present application, before flowing the second polar medium through the biochip device, the method further includes flowing air through the biochip device to replace at least part of the second non-polar medium.

A fifth aspect of embodiments of the present application provide a sequencing device, including the biochip device as described above and a membrane layer prepared by the membrane forming method as described above.

The hole array layered structure provided in the present application provides the side walls of the first holes to be closed, which can make the respective hole units relatively independent and reduce the movement of the mediums among the respective hole units after the membrane formation, especially when the membrane in the hole unit breaks, the polar solvent below the membrane in the hole unit diffuses into other hole units along the first hole and further affecting the stability of other hole units.

BRIEF DESCRIPTION OF THE DRAWINGS

In order to more clearly explain the technical solution of the embodiments of the present application, the accompanying drawings needed in the embodiments of the present application will be briefly introduced below. It is obvious that the accompanying drawings described below are only some embodiments of the present application, and the person skilled in the art can obtain other accompanying drawings from these accompanying drawings without expending creative work.

FIG. 23 is a flow chart of an embodiment of a precoating method in the present application;

FIG. 24 is a flow chart of an embodiment of an evaporation-condensation process in the present application;

FIG. 29 is a flowchart of another embodiment of the precoating method in the present application;

FIG. 30 is a schematic diagram of implementing the embodiment shown in FIG. 29;

FIG. 31 is a flowchart of another embodiment of the precoating method in the present application;

FIG. 32 is a schematic diagram of implementing the embodiment shown in FIG. 31;

FIG. 33 is a flowchart of an embodiment of a membrane forming method in the present application;

FIG. 37 is a flowchart of another embodiment of the membrane forming method in the present application;

BEST EMBODIMENTS OF THE PRESENT DISCLOSURE

The features and exemplary embodiments of various aspects of the present application will be described in detail below. In the following detailed description, many specific details are proposed to provide a comprehensive understanding of the present application. However, it is obvious to the person skilled in the art that the present application can be implemented without some of these specific details. The following description of the embodiments is only to provide a better understanding of the present application by showing examples of the present application.

The orientation terms in the description of the present application are merely for the convenience of describing the present application and simplifying the description, but not for indicating or implying that the device or element referred to must have a specific orientation, be constructed and operated in a specific orientation, and therefore cannot be understood as limitations to the present application.

It should be noted that the embodiments of the present application and the features in the embodiments can be combined with each other in case that there is no conflict. The embodiments will be described in detail in combination with the accompanying drawings.

Figure 1:
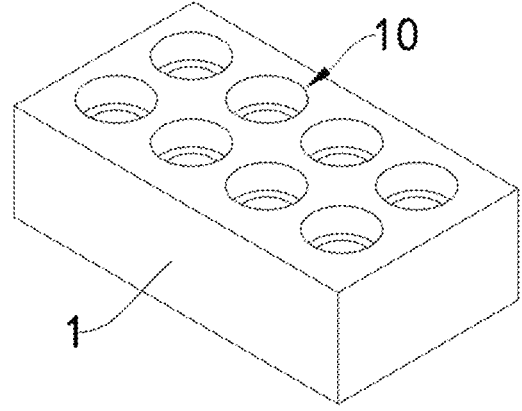
FIG. 1 is a schematic diagram of an array of a hole array layered structure provided by an embodiment of the present application.
Figure 2:
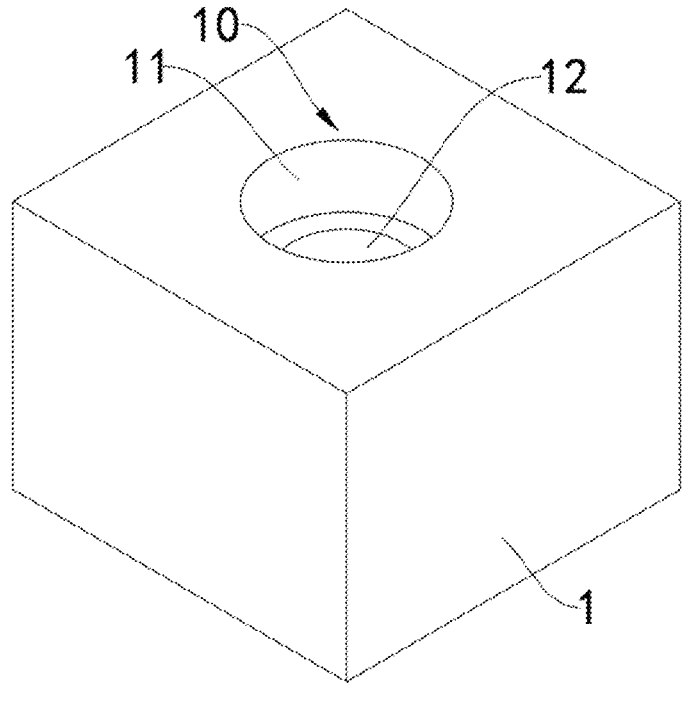
FIG. 2 is a structural schematic diagram of a hole array layered structure provided by an embodiment of the present application.
Figure 3:
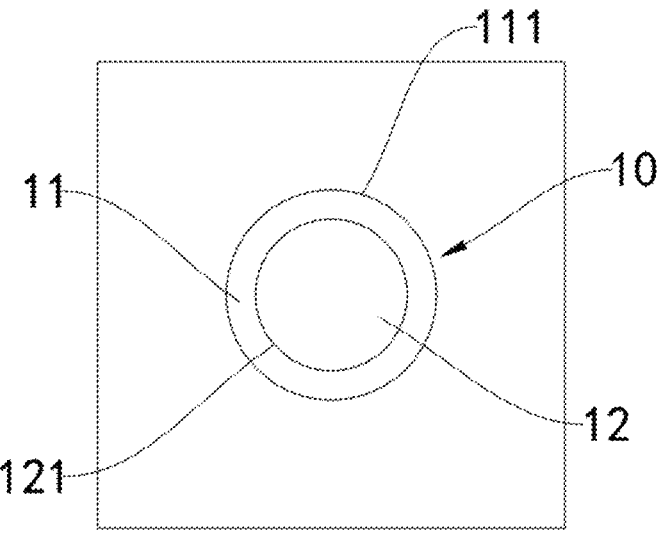
FIG. 3 is a structural schematic diagram of the embodiment shown in FIG. 2 in a top view.

In some optional embodiments of the embodiments of the present application, as shown in FIGS. 1 to 3, a hole array layered structure is provided, which is adapted to form a membrane forming space with a substrate, and the membrane forming space is adapted to form a membrane layer. The hole array layered structure includes a base plate 1, a plurality of hole units are arranged in the base plate 1 in an array, the hole units penetrate through the base plate 1, and each hole unit includes a first hole 11 and a second hole 12 stacked along a thickness direction of the base plate 1. The second hole 12 is configured to be connected with the substrate, a projection of the first hole 11 on a plane perpendicular to the thickness direction of the base plate 1 has a first hole contour 111, a projection of the second hole 12 on a plane perpendicular to the thickness direction of the base plate 1 has a second hole contour 121, and the first hole contour 111 surrounds the second hole contour 121 on an outer side thereof; the second holes 12 of the hole units are disconnected with each other, so as to prevent polar medium from flowing among the second holes 12, and the first holes 11 of the plurality of hole units are disconnected with each other, so as to prevent non-polar medium from flowing among the plurality of first holes 11.

Optionally, the first hole contour 111 may be in a shape of a circle, and exemplarily, a diameter of the first hole contour 111 may be 20 μm to 200 μm, for example, may be 20 μm, 50 μm, 80 μm, 100 μm, 120 μm, 150 μm or 200 μm, or the like, which is conducive to improving a membrane-forming rate and a membrane-forming quality of a molecular membrane. In practice, an amphiphilic molecular membrane can be formed substantially at an interface of the first hole 11 and the second hole 12, and under the action of electrodes, a potential difference can be generated between an upper side and a lower side of the base plate, so that there is a current flowing through the hole unit. When a single-stranded DNA passes through the hole unit, due to different structures of different basic groups on the single-stranded DNA, different interactions with the protein hole will occur, resulting in changes of an electrical resistivity of the nanopore and then causing changes of the current, thereby converting the basic group information on the single-stranded DNA to electrical signals. Measuring change amount of the current can identify the basic group information on the single-stranded DNA and thus the gene sequencing is completed. Optionally, in the thickness direction of the base plate 1, the first hole 11 and the second hole 12 have an equal depth.

A side wall of the first hole 11 is formed to be closed, which can make the respective hole units relatively independent from each other, so that the polar medium and non-polar medium in the first holes 11 cannot move among the respective hole units after the membrane is formed, especially when the molecular membrane in a certain hole unit breaks, the polar solvent below the membrane will contact and fuse with the polar solvent above the membrane, the polar medium will occupy the original position of the non-polar medium in the hole unit, and in such process, the non-polar medium may be absorbed from adjacent hole units, which causes a chain breaking of the molecular membranes in the connected hole units, and seriously affects the stability of the molecular membranes.

Figure 4:
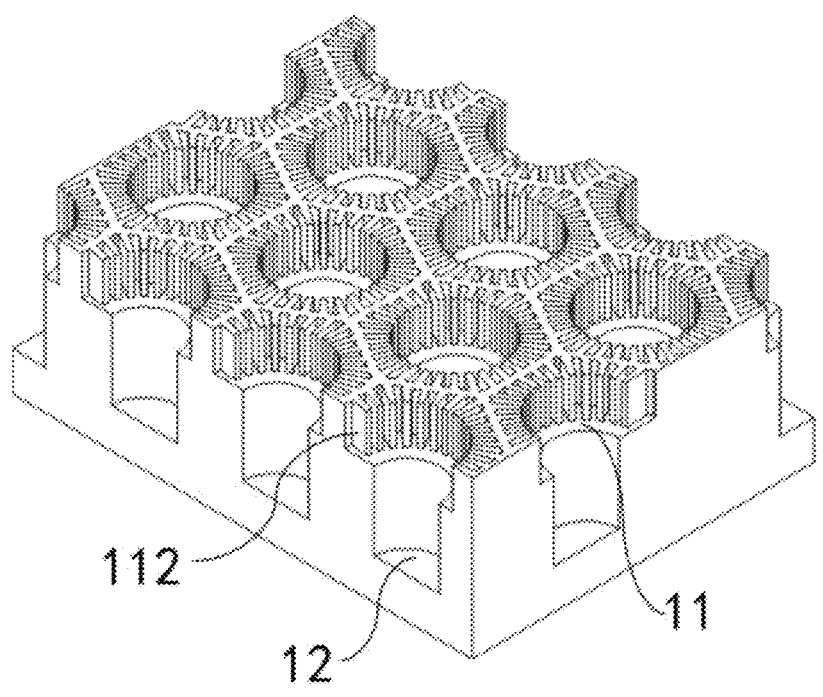
FIG. 4 is a schematic diagram of an array of a hole array layered structure provided by another embodiment of the present application.
Figure 5:
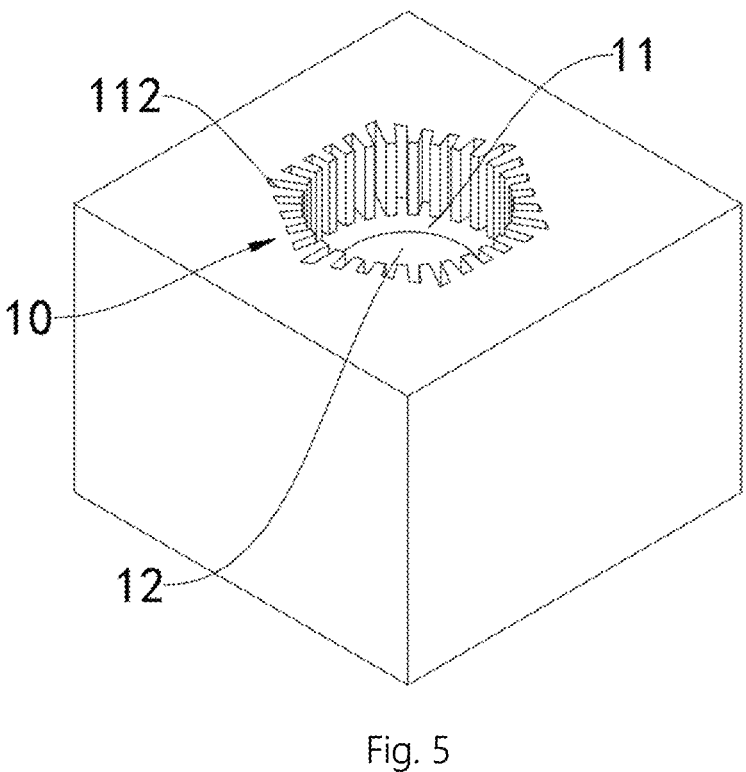
FIG. 5 is a structural schematic diagram of a hole array layered structure provided by another embodiment of the present application.
Figure 6:
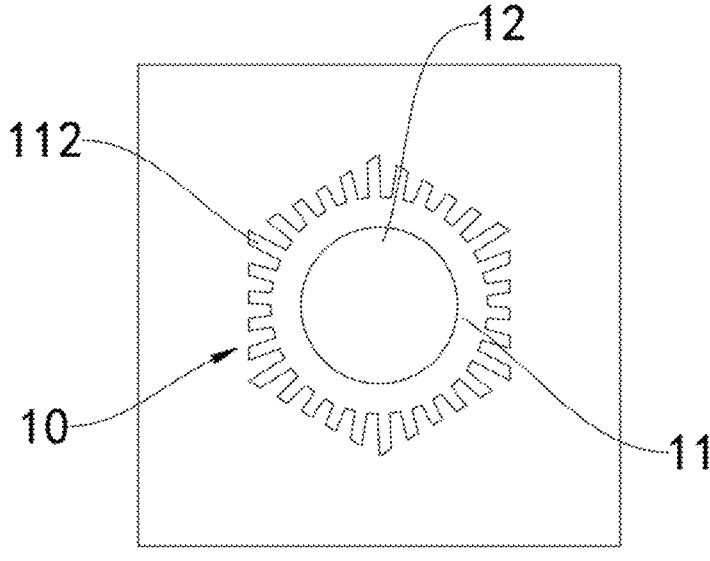
FIG. 6 is a structural schematic diagram of the embodiment shown in FIG. 5 in a top view.

In some optional embodiments of the present application, as shown in FIGS. 4 to 6, the hole array layered structure further includes first tooth slots 112 extending outward from the side wall of the first hole 11 perpendicularly to the thickness direction of the base plate 1. A plurality of first tooth slots 112 is provided in a circumferential direction of the first hole 11, and each of the first tooth slots 112 has an opening communicated with the first hole 11 at the first hole contour 111. In the projection on the plane perpendicular to the thickness direction of the base plate 1, extension lengths from slot bottoms to the openings of the respective first tooth slots 112 are different.

Optionally, the first tooth slots 112 extend in the thickness direction of the base plate 1 with a distance the same as the depth of the first hole 11. Optionally, the first tooth slots 12 may each have a uniform width from the opening to the slot bottom, and for example, the width of each first tooth slot 12 is equal or increases or decreases proportionally in a linear relationship from the opening to the slot bottom. Optionally, the first tooth slots 112 may each have non-uniform width from the opening to the slot bottom, and for example, the width of each first tooth slot 112 increases at first and then decreases from the opening to the slot bottom.

By providing the first tooth slots 112, when the first hole 11 contains the non-polar medium, the non-polar medium will be stored in the first tooth slots 112 through capillary action, and secondly, the amphiphilic molecular membrane formed in the first hole 11 can also tend to aggregation through sharp-angle or right-angle structures on the first tooth slots 112, so that the first hole 11 can pull the molecular membrane relatively stably and can support the molecular membrane more stably, thereby effectively improving the membrane-forming rate and the stability after membrane formation. Secondly, the arrangement of the first tooth slots 112 extending in different lengths perpendicular to the thickness direction of the base plate 1 makes the surface of the base plate 1 have different permeability, facilitating the fluid on the surface of the base plate 1 to permeate into the first tooth slots 112 more quickly, and then enter the first holes 11.

In some embodiments, any number of hole units can be provided on the base plate 1. Optionally, hole units such as 2 to 106 hole units, can be provided on the base plate 1. In some embodiments, the polar medium may be hydrophilic medium, such as aqueous solution of buffer agent, and the buffer agent may include supporting electrolyte.

In some embodiments, the non-polar medium may be hydrophobic medium, such as hydrocarbon-containing substance, oily substance or mixture of the two. The hydrophobic medium can be one or more of silicone oil, AR20 and hexadecane. The non-polar medium can be immiscible with the polar medium, and the non-polar medium contains amphiphilic molecules, for forming the amphiphilic molecular membrane when the polar medium contacts with the non-polar medium.

Figure 7:
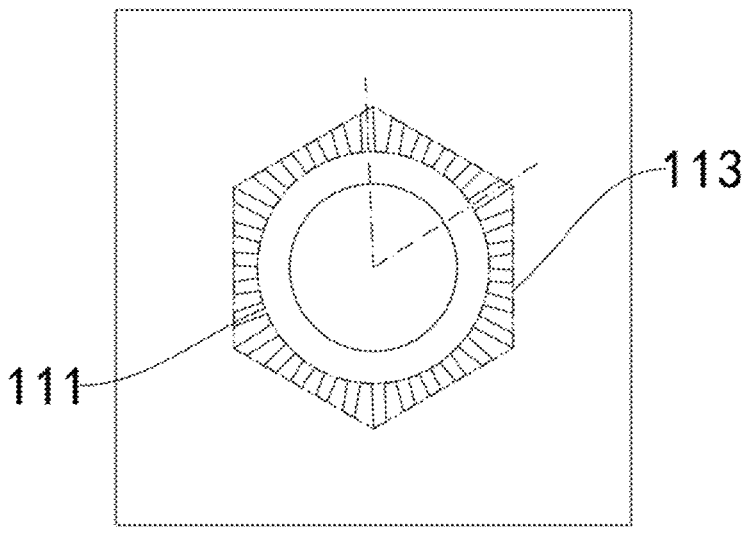
FIG. 7 is a structural schematic diagram showing axes of first tooth slots, a first tooth slot outer contour and a first hole contour by adding auxiliary lines.

In some optional embodiments of the present application, as shown in FIG. 7, on a plane perpendicular to the thickness direction of the base plate 1, a contour constrained by projections of the slot bottoms of plurality of first tooth slots 112 and extension lines thereof is a first tooth slot outer contour 113, and the first tooth slot outer contour 113 is in a shape of a regular polygon or a circle.

Exemplarily, on the plane perpendicular to the thickness direction of the base plate 1, the first tooth slot outer contour 113 may further be provided in a petal shape.

By constraining the first tooth slot outer contour 113, it is convenient to arrange the hole units on the base plate 1, make boundaries between adjacent hole units clearer, and prevent the communication between adjacent hole units. By reasonably arranging the hole units according to the first tooth slot outer contour 113, as many hole units as possible can be provided on the base plate 1 by minimizing areas between the hole units on the surface of the base plate 1 as much as possible.

Figure 8:
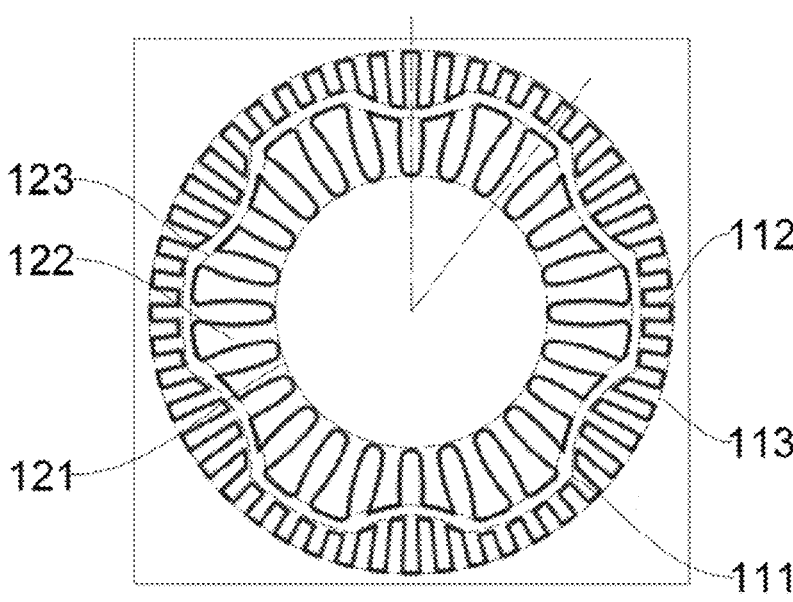
FIG. 8 is a schematic diagram of a hole array layered structure in a top view provided by a further embodiment of the present application.
Figure 9:
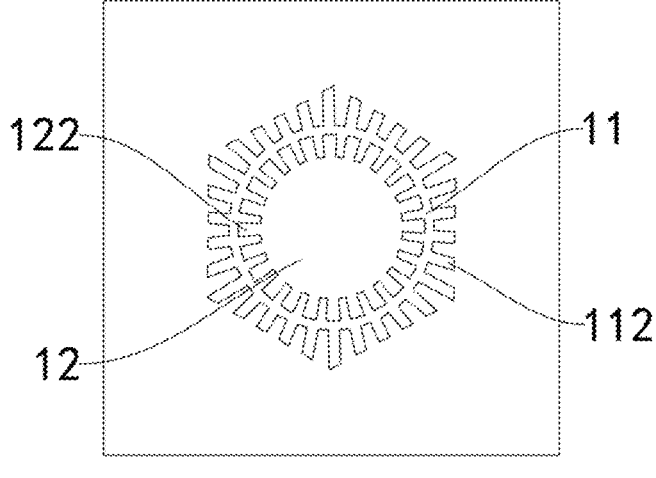
FIG. 9 is a structural schematic diagram of the embodiment shown in FIG. 8 wherein the first tooth slot outer contour is transformed into a regular hexagon.
Figure 10:
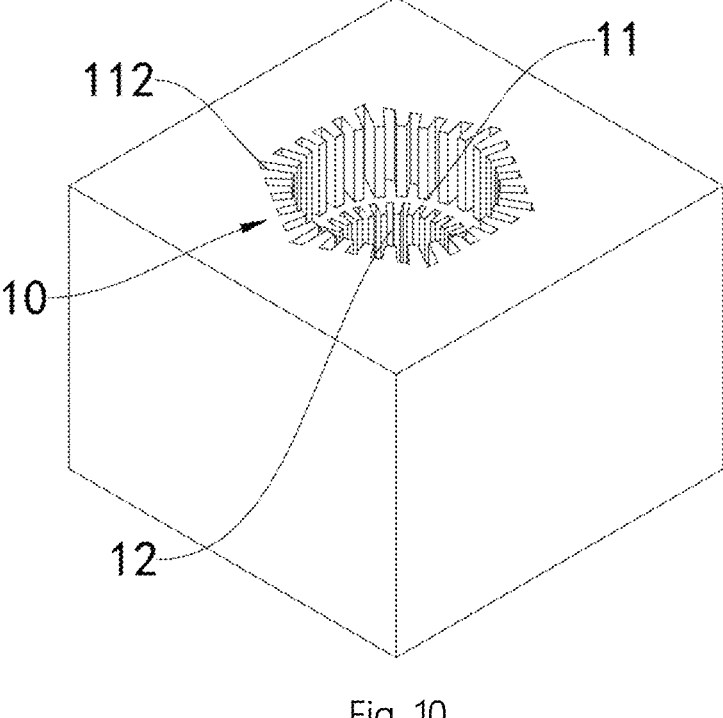
FIG. 10 is a three-dimensional structural diagram of the embodiment shown in FIG. 9.
Figure 11:
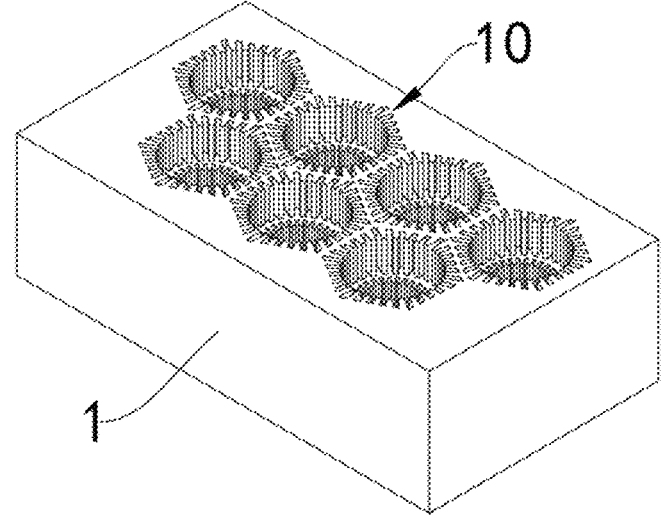
FIG. 11 is an array schematic diagram of the embodiment shown in FIG. 9.

In some optional embodiments of the present application, as shown in FIGS. 7 and 8, on the plane perpendicular to the thickness direction of the base plate 1, axes of the plurality of first tooth slots 112 extend and then intersect at a center of the first tooth slot outer contour 113.

Exemplarily, when the first tooth slot outer contour 113 is formed as a circle, the axes of the plurality of first tooth slots 112 coincide with radiuses of the circle. Optionally, when the first tooth slot outer contour 113 is formed as a circle, axes of the first tooth slots 112 can be set in non-radial directions of the circle.

Optionally, the number of sides of the first tooth slot outer contour 113 depends on the number of adjacent hole units around the hole unit in the array structure. Optionally, on the plane perpendicular to the thickness direction of the base plate 1, the plurality of first tooth slots 112 have different extension lengths, and thus spaces between the plurality of first tooth slots 112 can be provided to different lengths. For example, the first tooth slot outer contour 113 can be a regular hexagon, and the length of the space between the first tooth slots 112 at each vertex of the regular hexagon is the longest, that is, the slot bottom of the first tooth slot 112 at this position is farthest from the center of the first hole 11, while the space between the first tooth slots 112 at the center of each side of the regular hexagon is the shortest, that is, the slot bottom of the first tooth slot 112 at this location is closest to the center of the first hole 11. Therefore, when the first tooth slot outer contour 113 is a regular hexagon, the lengths of the spaces between the first tooth slots 112 increase gradually from the center of each side of the regular hexagon to two vertexes of the side.

By overlapping the intersection point of the axes of the plurality of first tooth slots 112 with the center of the first tooth slot outer contour 113, the contour of the first hole 11 can be made more regular, which not only facilitates the arrangement of the hole units, but also makes the hole units have the characteristics of central symmetry, so that the pulling ability of each part on the hole unit to the medium is also central symmetry, effectively improving the membrane-forming efficiency and stability after membrane formation; secondarily, the first tooth slots 112 are made to have the characteristics of scattering around and facilitate the medium permeation.

In some optional embodiments of the present application, as shown in FIGS. 8 to 11, the hole array layered structure further includes second tooth slots 122 extending outward from a side wall of the second hole 12 perpendicularly to the thickness direction of the base plate 1, a plurality of second tooth slots 122 are provided in a circumferential direction of the second hole 12, and each second tooth slot 122 has an opening communicated with the second hole 12 at the second hole contour 121.

Optionally, the second tooth slots 122 extend in the thickness direction of the base plate 1 with a distance equal to the depth of the second hole 12.

By providing the second tooth slots 122, when the second hole 12 contains the non-polar medium during precoating of the non-polar medium on the hole unit, the non-polar medium will be stored in the second tooth slots 122 by capillary action; and when forming the amphiphilic molecular membrane, trend of aggregation can be generated by means of sharp-angle or right-angle structures on the second tooth slots 122, thereby maintaining the stability in the second hole 12, and improving the stability after membrane formation.

Figure 12:
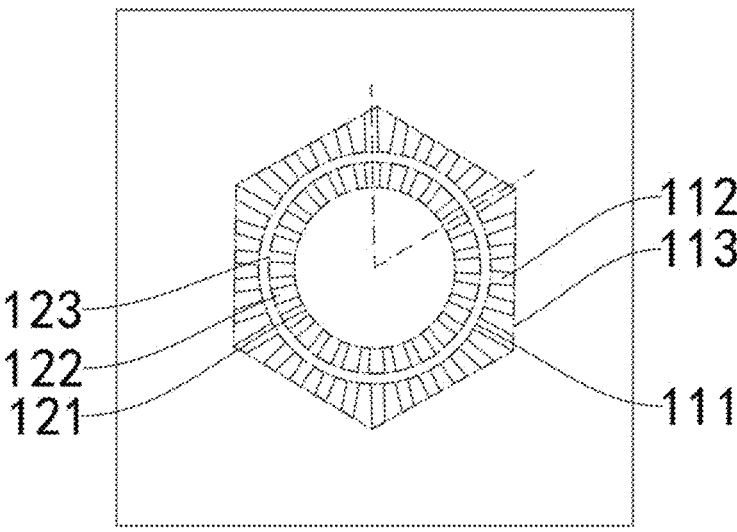
FIG. 12 is a structural schematic diagram showing axes of second tooth slots, a first hole contour, a first tooth slot outer contour, a second hole contour and a second tooth slot outer contour by adding auxiliary lines.

In some optional embodiments of the present application, as shown in FIG. 12, on the plane perpendicular to the thickness direction of the base plate 1, a contour constrained by projections of the openings of the plurality of first tooth slots 112 and extension lines thereof is the first hole contour 111, a contour constrained by projections of slot bottoms of the plurality of second tooth slots 122 and extension lines thereof is a second tooth slot outer contour 123, and the second tooth slot outer contour 123 is consistent with the first hole contour 111.

Specifically, the second tooth slot outer contour 123 can be obtained by scaling the first hole contour 111, and vertical lines from various points on the second tooth slot outer contour 123 to the first hole contour 111 are equal. Exemplarily, when the first hole contour 111 is in a shape of a circle, the second tooth slot outer contour 123 is in a shape of a circle, and is concentric with the first hole contour 111.

By providing the second tooth slot outer contour 123 as described above, the second tooth slots 122 can be facilitated to extend within the second hole 12 as close as possible to the first hole contour 111, so that the second tooth slots 122 can extend at a better depth in the plane perpendicular to the thickness direction of the base plate 1, thereby improving the efficiency of the medium fluid entering the second tooth slots 122.

In some optional embodiments of the present application, as shown in FIG. 12, when the first tooth slot outer contour 113 is in a shape of a regular polygon, the first hole contour 111 is in a shape of a circle, and the center of the first tooth slot outer contour 113 coincides with the center of the first hole contour 111.

Figure 13:
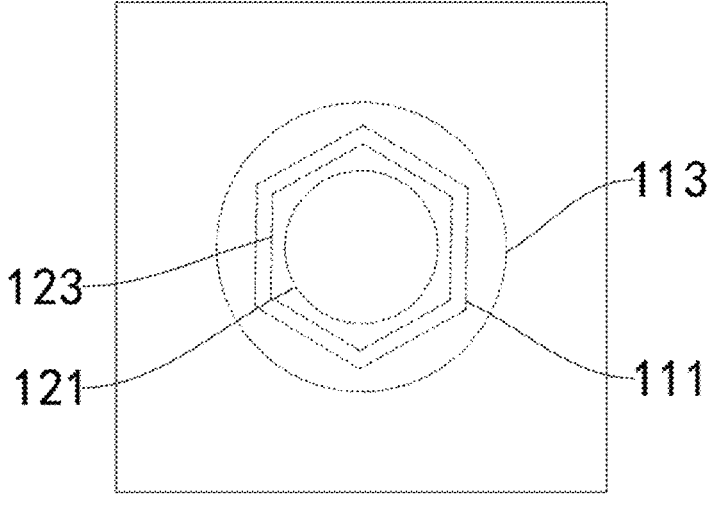
FIG. 13 is a schematic diagram showing shapes of a first hole contour, a first tooth slot outer contour, a second hole contour and a second tooth slot outer contour in an optional embodiment of the present application.

In some optional embodiments of the present application, as shown in FIG. 13, when the first tooth slot outer contour 113 is in a shape of a circle, the first hole contour 111 is non-circular, and the center of the first tooth slot outer contour 113 coincides with the center of the first hole contour 111.

In some optional embodiments of the present application, as shown in FIG. 13, on the plane perpendicular to the thickness direction of the base plate 1, a contour constrained by projections of the openings of the second tooth slots 122 and extension lines thereof is the second hole contour 121, the second hole contour 121 is located within the first hole contour 111, the second hole contour 121 is in a shape of a circle, and the center of the first tooth slot outer contour 113 coincides with a center of the second hole contour 121.

Figure 14:
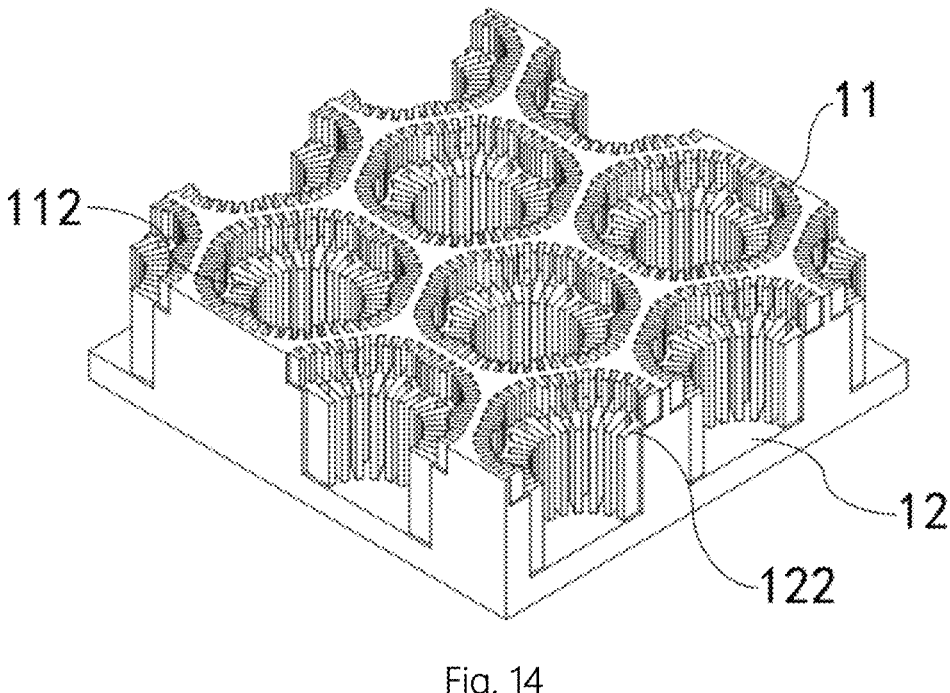
FIG. 14 is a structural schematic diagram of a hole array layered structure provided by another further embodiment of the present application.
Figure 15:
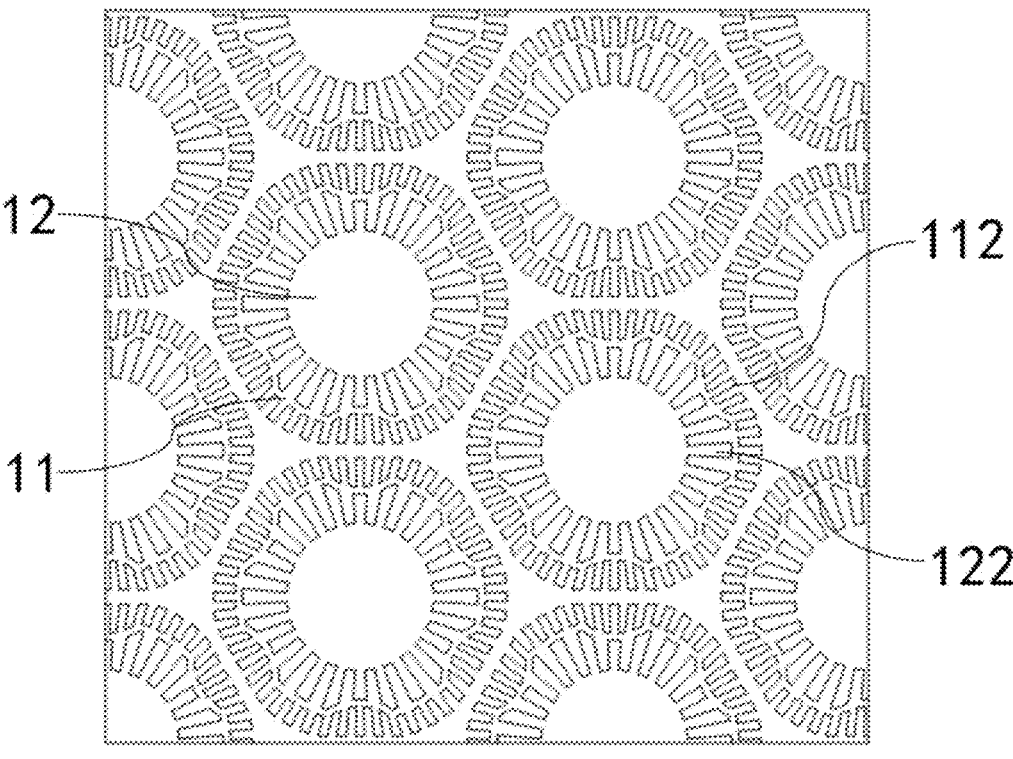
FIG. 15 is a structural schematic diagram of the embodiment shown in FIG. 14 in a top view.

Optionally, the first hole contour 111 and the second hole contour 121 may be in shapes of circles, the first tooth slot outer contour 113 and the second tooth slot outer contour 123 may be in shapes of regular hexagons, and the centers of the first hole contour 111, the second hole contour 121, the first tooth slot outer contour 113 and the second tooth slot outer contour 123 coincide with each other. Optionally, the first hole contour 111, the second hole contour 121, the first tooth slot outer contour 113 and the second tooth slot outer contour 123 are all center-symmetric patterns, and the aforementioned centers are centers of symmetry. Exemplarily, referring to FIG. 14 and FIG. 15, the first hole contour 111, the first tooth slot outer contour 113 and the second tooth slot outer contour 123 are in hexagon-like shapes rounded at angles, and the second hole contour 121 is in a shape of a circle.

In some optional embodiments of the present application, as shown in FIG. 13, on the plane perpendicular to the thickness direction of the base plate 1, axes of the plurality of second tooth slots 122 extend and then intersect at the center of the second hole contour 121.

Specifically, when the second hole contour 121 is in a shape of a circle, the axes of the second tooth slots 122 coincide with radiuses of the circle.

Figure 16:
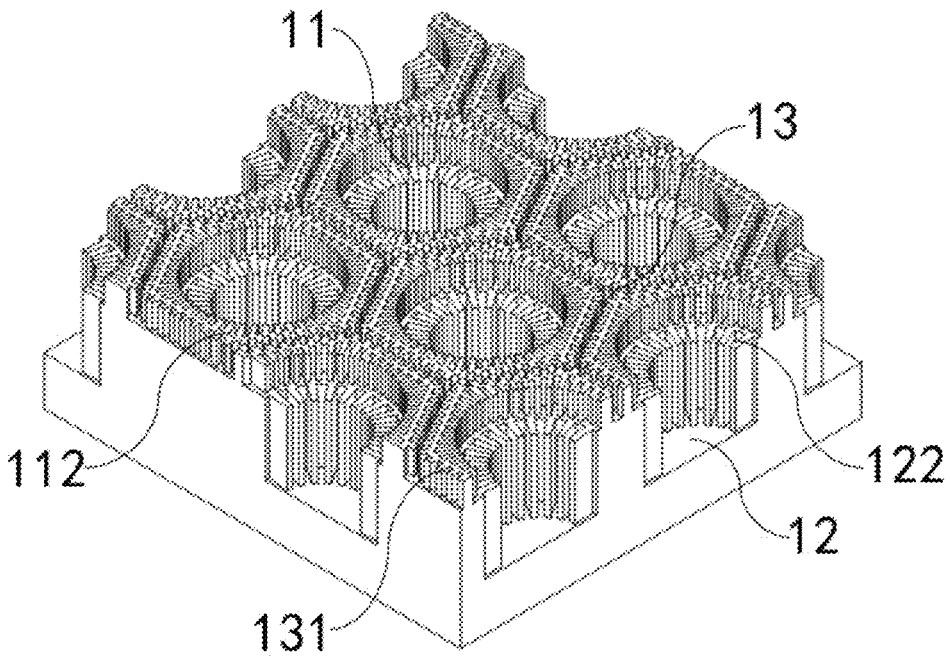
FIG. 16 is a schematic diagram of an array of a hole array layered structure provided by an optional embodiment of the present application.
Figure 17:
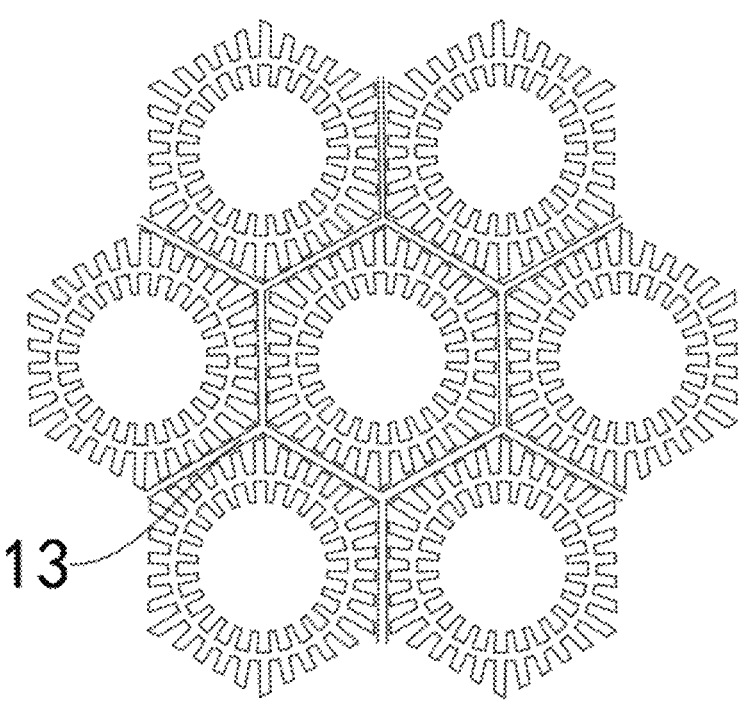
FIG. 17 is a structural schematic diagram of a hole array layered structure in a top view provided by an optional embodiment of the present application.

In some optional embodiments of the present application, as shown in FIG. 16 and FIG. 17, a plurality of hole units are provided in the base plate 1, and channels 13 are further provided between adjacent hole units; the channels 13 extend along the thickness direction of the base plate 1, and on the plane perpendicular to the thickness direction of the base plate 1, projections of the channels 13 are consistent with the projections of the first tooth slot outer contours 113.

Specifically, when the first tooth slot outer contour 113 is in a shape of a circle, or when the first tooth slot outer contour 113 is in a shape of a regular hexagon, the channels 13 are formed as a honeycomb which is formed by the regular hexagons that surround the first tooth slot outer contours 113.

By providing the channels 13 as described above, not only the respective hole units can be separated and thus the possibility of mutual influence between adjacent hole units is reduced, but also the reserved area of the surface of base plate 1 on a side of openings of the hole units can be reduced, thereby reducing the amount of fluid left on the surface of base plate 1 on the side of openings of the hole units, and preventing a subsequent coating process from being affected by the medium left in a previous step when multiple fluids are sequentially coated on the hole units.

Figure 18:
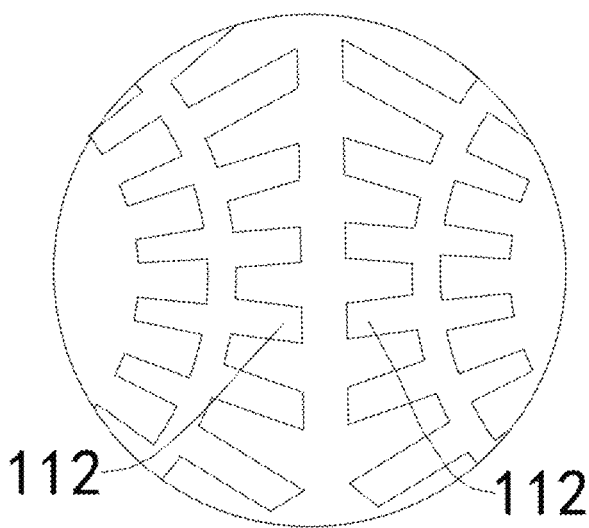
FIG. 18 is a partial structural schematic diagram in a top view of an array in an embodiment without channels.
Figure 19:
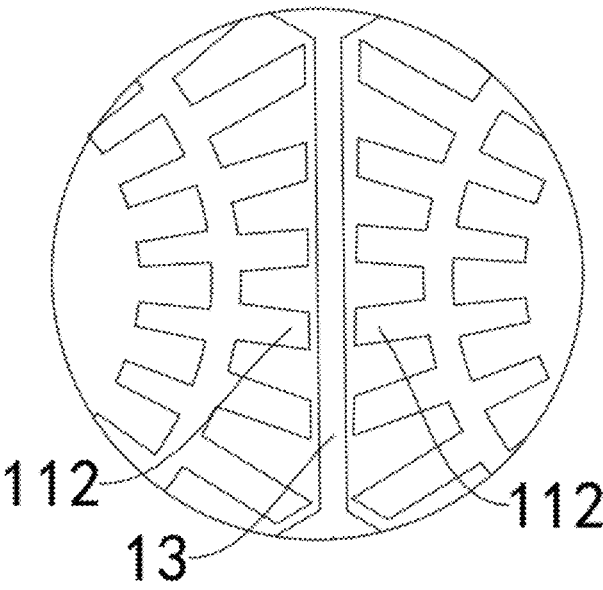
FIG. 19 is a first partial structural schematic diagram of the embodiment shown in FIG. 17 in a top view.

In some optional embodiments of the present application, as shown in FIG. 18 and FIG. 19, in the hole array layered structure, the first tooth slots 112 of one of the plurality of hole units are aligned with the first tooth slots 112 of adjacent hole units.

Optionally, the slot bottoms of the plurality of first tooth slots 112 on adjacent hole units are arranged correspondingly.

Figure 20:
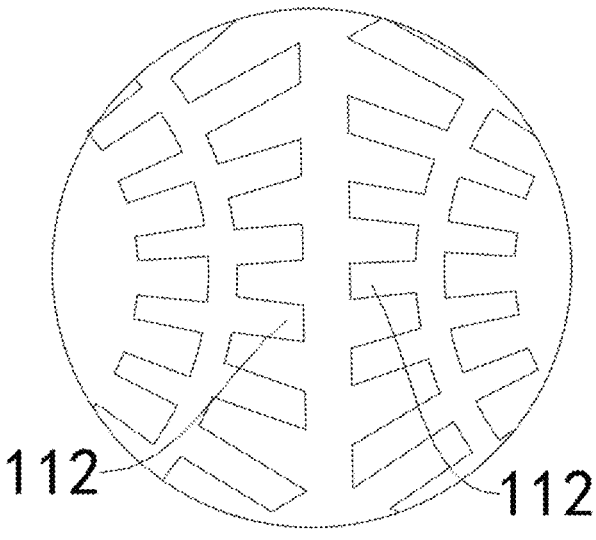
FIG. 20 is a partial structural schematic diagram of an array in a top view according to another embodiment without channels.
Figure 21:
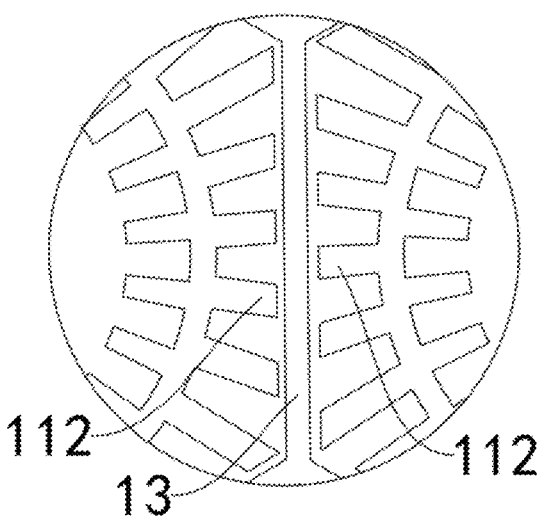
FIG. 21 is a second partial structural schematic diagram in a top view of the embodiment shown in FIG. 17.

In some optional embodiments of the present application, as shown in FIG. 20 and FIG. 21, in the hole array layered structure, the first tooth slots 112 of one of the plurality of hole units are staggered with the first tooth slots 112 of adjacent hole units.

Specifically, the slot bottoms of the plurality of first tooth slots 112 on one of the hole units corresponds to the openings of a plurality of first slots 112 on the adjacent hole units.

Figure 22:
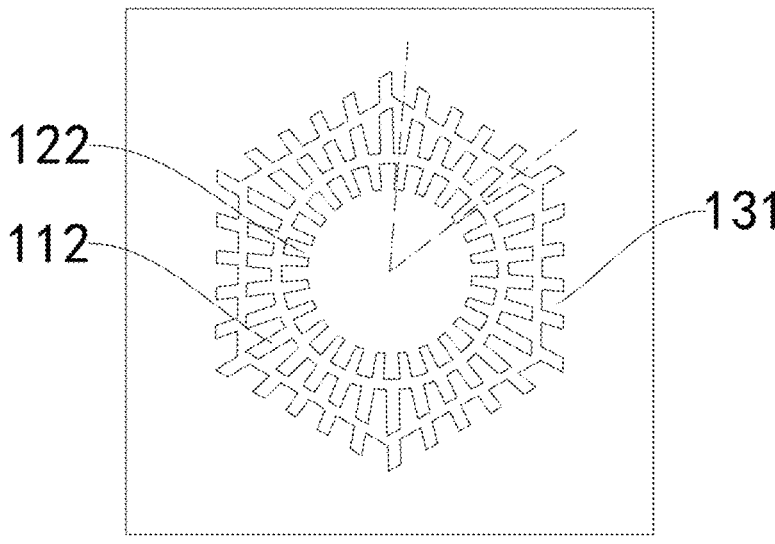
FIG. 22 is a structural schematic diagram showing axes of third tooth slots by adding auxiliary lines.

In some optional embodiments of the present application, as shown in FIG. 16 and FIG. 22, side walls of channels 13 are provided with a plurality of third tooth slots 131 which extend outward in the direction perpendicular to the thickness of base plate 1.

Optionally, the third tooth slots 131 may be aligned with adjacent first tooth slots 112, that is, slot bottoms of the third slots 131 are parallel and correspond to the slot bottoms of the adjacent first tooth slots 112. Optionally, the third tooth slots 131 may be staggered with adjacent first tooth slots 112, that is, the slot bottoms of the third tooth slots 131 are parallel and correspond to tooth ends of the adjacent first tooth slots 112.

By providing the third tooth slots 131 as described above, after the fluid is coated, the medium remaining on the base plate 1 on the side of the openings of the hole units can rapidly permeate into the channels 13 through the capillary action of the third tooth slots 131 and thus and be discharged, thereby being prevented from affecting subsequent operations.

In some optional embodiments of the present application, as shown in FIG. 22, on the plane perpendicular to the thickness direction of the base plate 1, axes of the plurality of third tooth slots 131 extend and then intersect at the center of the first tooth slot outer contour 113.

Exemplarily, when the first tooth slot outer contour 113 is in a shape of a circle, the axes of the plurality of third tooth slots 131 coincide with radial directions of the circle.

By overlapping the intersection point of the axes of the plurality of third tooth slots 131 with the center of the first tooth slot outer contour 113, the reserved area of the base plate 1 on the side of openings of the hole units and the channels 13 can be more evenly distributed, thereby facilitating the residual medium on the reserved area entering the channels 13.

In some optional embodiments of the present application, a biochip device 100 is provided, including a substrate and the hole array layered structure 1. The hole array layered structure is located on the substrate, and the first holes 11 of the hole units 10 are located on a side of the second holes 12 of the hole units 10 facing away from the substrate.

Figure 25:
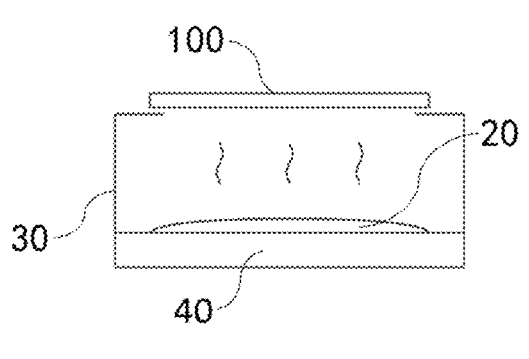
FIG. 25 is a schematic diagram of implementing the embodiment shown in FIG. 24.
Figure 26:
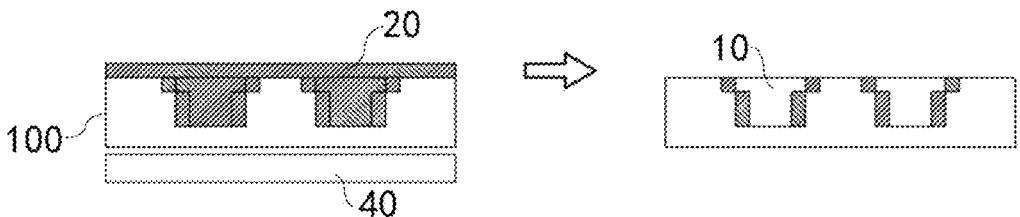
FIG. 26 is a schematic diagram of implementing an excessive precoating removal process in the present application.
Figure 27:
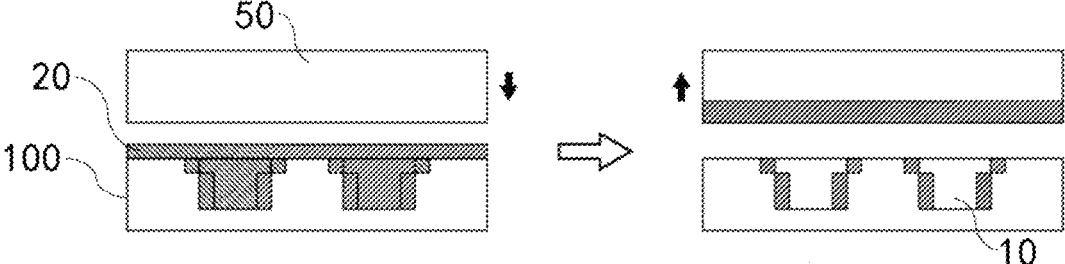
FIG. 27 is a schematic diagram of implementing an embodiment of the excessive precoating removal process in the present application.
Figure 28:
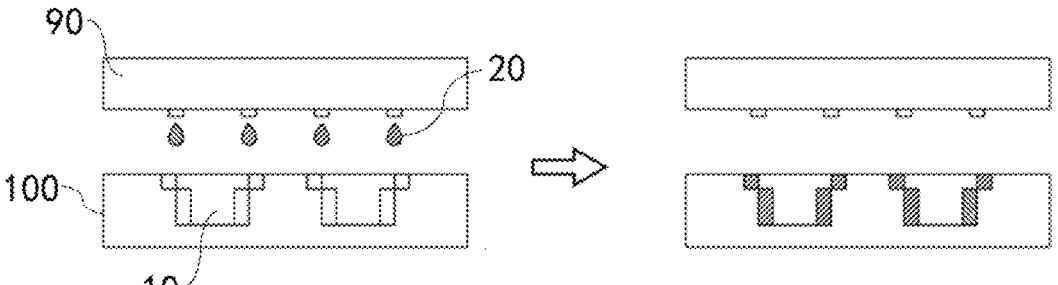
FIG. 28 is a schematic diagram of implementing a spray removal process in the present application.

In some optional embodiments of the present application, as shown in FIG. 23, a precoating method for a biochip device is provided, including the following steps:

S11. Providing the above-mentioned biochip device 100;

S12. Precoating the biochip device, the precoating including any of the following processes:

(1) an evaporation-condensation process, referring to FIG. 24 and FIG. 25, including S1211, orienting openings of the hole units 10 in the biochip device 100 towards an evaporation position; and S1212, providing a precoating means 30 which contains a precoating material 20, placing the precoating means 30 at the evaporation position with an opening of the precoating means 30 facing the biochip device 100, heating the precoating means 30 to an evaporation threshold, and stopping the precoating after heating for a predetermined time;

(2) an excessive precoating removal process, referring to FIG. 26 and FIG. 27, including: S1221, adding a precoating material 20 greater than a precoating threshold in the hole units 10; and S1222, removing the precoating material 20 in the hole units 10 to the precoating threshold;

(3) a spraying process, referring to FIG. 28, including: S1231, taking the biochip device 100 and a printer 90, wherein the printer 90 is provided with a precoating material 20; S1232, aligning printing heads of the printer 90 with edges of the hole units 10 on the biochip device 100; and S1233, starting the printer 90 and spraying a predetermined amount of the precoating material 20 into the hole units 10.

Optionally, the precoating material 20 may be a non-polar medium. In the evaporation-condensation process, the precoating means 30 can be a container containing the precoating material and provided with an opening, the opening is the evaporation position. The openings of the hole units 10 are disposed towards the opening of the precoating means 30. When heating the precoating means 30 and after the precoating material 20 is heated and evaporated, the precoating material 20 floats out through the opening of the precoating means 30, and condenses in the hole units 10 facing the opening of the precoating means, thereby realizing the precoating of the hole units 10.

Optionally, silicone oil AR20 can be used for the precoating material in the evaporation-condensation process. The openings of the hole units 10 are 5 to 10 cm away from a liquid level of a non-polar solvent. A heater 40 can be set at a temperature of 100 to 140° C. By continuously heating and condensing for 10 to 40 minutes, the precoating of the hole units 10 can complete.

Optionally, the silicone oil AR20 can be used for the precoating material 20 in the excess precoating removal process, and the excess precoating material 20 can be removed by heating at 120° C. for 30 minutes.

The biochip device 100 can be precoated so that the side walls of the first holes 11 and the second holes 12 in the hole units 10 are coated with the non-polar medium; in case that the side walls of the first holes 11 and the second holes 12 are provided with the first tooth slots 112 and the second tooth slots 122, the first tooth slots 112 and the second tooth slots 122 are coated with the non-polar medium, so as to facilitate the subsequent membrane formation.

In some optional embodiments of the present application, as shown in FIG. 25, the step S1222 in the excessive precoating removal process may include: heating the biochip device 100 by the heater 40 to evaporate the precoating material 20 until the precoating material 20 in the hole units 10 reaches the precoating threshold.

In some optional embodiments of the present application, as shown in FIG. 26, the step S1222 in the excessive precoating removal process may include: providing a suction means 50, covering the base plate 1 on a side of the openings of the hole units 10 by the suction means, adsorbing the precoating material 20 from the hole units 10 by the suction means 50 until the precoating material 20 in the hole units 10 reaches the precoating threshold. Specifically, the suction means 50 is made of materials that can absorb the non-polar medium.

In some optional embodiments of the present application, as shown in FIG. 29 and FIG. 30, a precoating method for a biochip device is further provided, and the method includes the following steps:

S21, providing the above-mentioned biochip device 100;
S22, providing a leaking plate 60 with leaking holes 601, and covering the biochip device 100 on a side of openings of the hole units 10 by the leaking plate 60 so that edges of the hole units 10 correspond to at least one leaking hole 601 on the leaking plate 60, wherein when the hole units 10 are provided with the first tooth slots 112, the leaking holes 601 are made to correspond to the first tooth slots 112, when the hole units 10 are provided with the first tooth slots 112 and the second tooth slots 122, the leaking holes 601 are made to correspond to the first tooth slots 112 and the second tooth slots 122, for example, the widths of the leaking holes 601 can be equal to widths from the bottoms of the first tooth slots 112 to the openings of the second tooth slots 122;
S23, providing a scraping means 70 so that an edge of the scraping means 70 is attached to a side of the leaking plate 60 facing away from the biochip device 100 and the scraping means 70 is movable relative to the leaking plate 60;
S24, taking a precoating material 20, placing it on one side of the leaking plate 60, and moving the scraping means 70 to push the precoating material 20 to move towards the other side of the leaking plate 60, wherein when a movement track of the precoating material 20 passes across respective leaking holes 601, the precoating material 20 enters the hole units 10 through the leaking holes 601, thereby achieving the precoating.

In some optional embodiments of the present application, as shown in FIG. 31 and FIG. 32, a precoating method for a biochip device is further provided, and the method includes the following steps:

S31, providing the above-mentioned biochip device 100;
S32, providing a printing plate 80, which is provided with a transfer portion, such as any surface on the printing plate 80 (in the example shown in FIG. 31, the transfer portion is located on a lower surface of the printing plate 80), wherein the printing plate 80 is movable relative to the biochip device 100, and when the printing plate 80 covers the biochip device 100 on a side of openings of the hole units 10, a portion of the printing plate 80 attached to the biochip device 100 is located in the transfer portion;
S33, taking a precoating material 20 and uniformly disposing the precoating material 20 on the transfer portion;
S34, performing transfer printing: covering the biochip device 100 on the side of the openings of the hole units 10 by the printing plate 80 provided with the precoating material 20 on its the transfer portion, transferring the precoating material 20 from the transfer portion of the printing plate 80 into the hole units 10 of the biochip device 100, and maintaining the covering state until the precoating material 20 in the hole units 10 reaches a precoating threshold.

Figure 34:
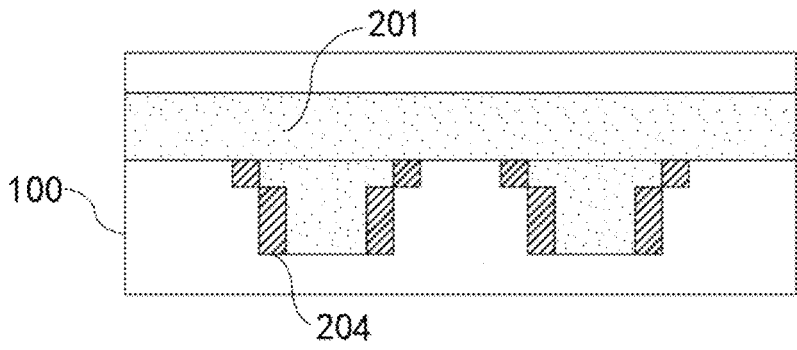
FIG. 34 is a schematic diagram of the implementation of step S43 in the embodiment shown in FIG. 33.
Figure 35:
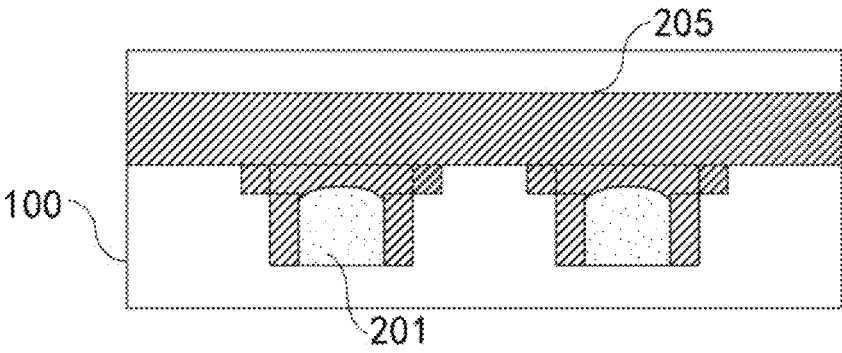
FIG. 35 is a schematic diagram of the implementation of step S44 in the embodiment shown in FIG. 33.
Figure 36:
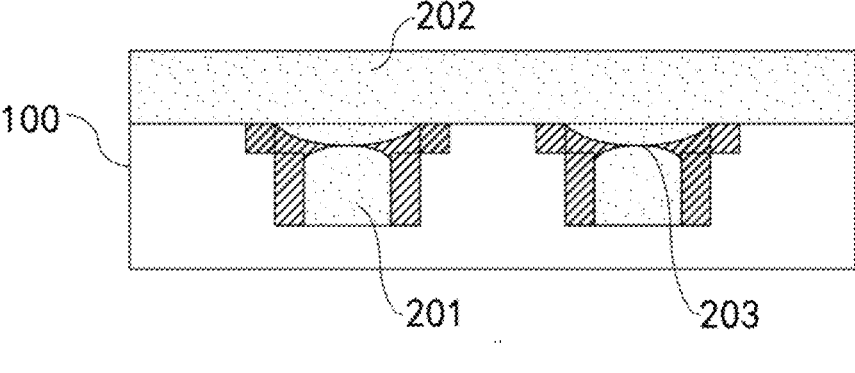
FIG. 36 is a schematic diagram of the implementation of step S45 in the embodiment shown in FIG. 33.

In some optional embodiments of the present application, as shown in FIG. 33, a membrane forming method is further provided, the method includes the following steps:

S41, providing the above-mentioned biochip device;
S42, arranging a first non-polar medium 204 in the biochip device 100 and forming a precoating membrane layer on a surface of the biochip device 100;
S43, as shown in FIG. 34, flowing a first polar medium 201 through the biochip device 100 so as to replace at least part of the first non-polar medium 204;
S44, as shown in FIG. 35, flowing a second non-polar medium 205 through the biochip device 100 so as to replace at least part of the first polar medium 201, wherein the second non-polar medium 205 contains amphiphilic molecular materials;
S45, as shown in FIG. 36, flowing a second polar medium 202 through the biochip device 100 so as to replace at least part of the second non-polar medium 205 and forming a membrane layer 203 at an interface between the first polar medium 201 and the second polar medium 202, wherein the membrane layer 203 contains amphiphilic molecular materials.

Figure 38:
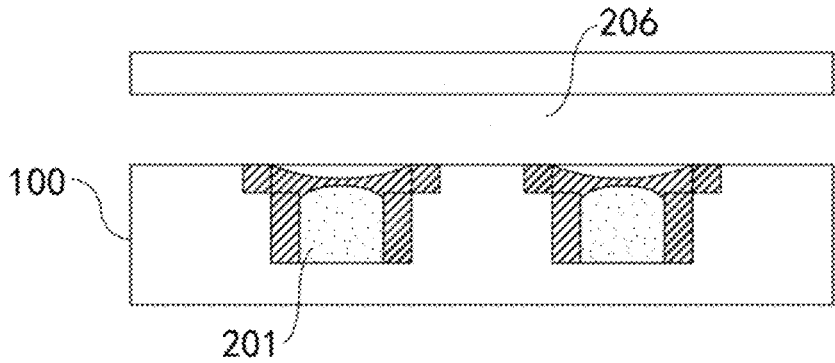
FIG. 38 is a schematic diagram of the implementation of step S441 in the embodiment shown in FIG. 37.
Figure 39:
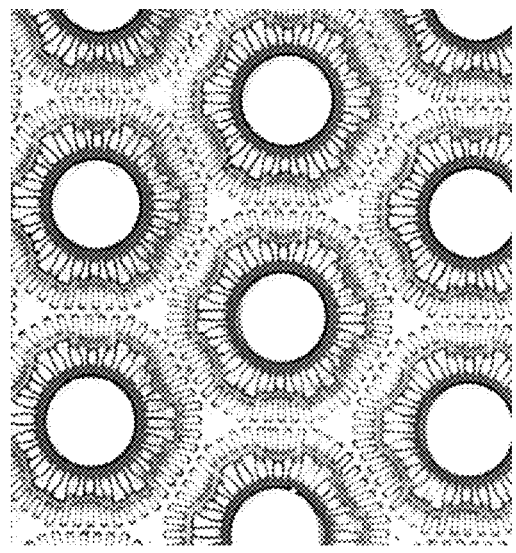
FIG. 39 is a schematic diagram of a structure in a top view after amphiphilic molecular membranes are formed.

In some optional embodiments of the present application, as shown in FIG. 37 and FIG. 38, before flowing the second polar medium 202 through the biochip device 100, the method further includes a step S441: flowing air 206 through the biochip device 100 to replace at least part of the second non-polar medium 205. In some optional embodiments of the present application, a sequencing device is further provided, as shown in FIG. 39, which includes the above-mentioned biochip device 100 and a membrane layer prepared by the membrane forming method.

Although the present application has been described with reference to the preferred embodiments, without departing from the scope of the present application, various improvements can be made and components can be replaced with equivalents. In particular, as long as there is no structural conflict, the various technical features mentioned in various embodiments can be combined in any manner. The present application is not limited to the specific embodiments disclosed herein, but includes all technical solutions falling within the scope of the claims.

What is claimed is:

1. A hole array layered structure for forming a membrane forming space with a substrate, wherein the membrane forming space is adapted to form a membrane layer, and the hole array layered structure comprises:

a base plate; and a plurality of hole units provided in the base plate and arranged in an array, each hole unit penetrating through the base plate and comprising a first hole and a second hole stacked in a thickness direction of the base plate, the second hole being configured to be connected with the substrate, a projection of the first hole on a plane perpendicular to the thickness direction of the base plate having a first hole contour, a projection of the second hole on the plane perpendicular to the thickness direction of the base plate having a second hole contour, the first hole contour surrounding the second hole contour on an outer side thereof, first tooth slots extending outward from a side wall of the first hole perpendicularly to the thickness direction of the base plate, the first tooth slots provided in a circumferential direction of the first hole, each of the first tooth slots has an opening communicated with the first hole at the first hole contour, and in a projection on the plane perpendicular to the thickness direction of the base plate, extension lengths from slot bottoms to the openings of the respective first tooth slots are different, the second holes of the plurality of hole units are disconnected with each other to prevent mediums in the respective second holes from flowing among the second holes, and the first holes of the plurality of hole units are disconnected with each other to prevent mediums in the respective first holes from flowing among the first holes.

2. The hole array layered structure according to claim 1, wherein, in each hole unit, on the plane perpendicular to the thickness direction of the base plate, a contour constrained by projections of the slot bottoms of the first tooth slots and extension lines thereof is defined as a first tooth slot outer contour, and the first tooth slot outer contour is in a shape of a regular polygon or a circle.

3. The hole array layered structure according to claim 2, wherein, in each hole unit, on the plane perpendicular to the thickness direction of the base plate, axes of the first tooth slots extend and intersect at a center of the first tooth slot outer contour.

4. The hole array layered structure according to claim 3, wherein each hole unit further comprising second tooth slots extending outward from a side wall of the second hole perpendicularly to the thickness direction of the base plate, the second tooth slots are provided in a circumferential direction of the second hole, and each of the second tooth slots has an opening communicated with the second hole at the second hole contour.

5. The hole array layered structure according to claim 4, wherein, in each hole unit, on the plane perpendicular to the thickness direction of the base plate, a contour constrained by projections of the openings of the first tooth slots and extension lines thereof is the first hole contour, a contour constrained by projections of slot bottoms of the second tooth slots and extension lines thereof is defined as a second tooth slot outer contour, and the second tooth slot outer contour is consistent with the first hole contour.

6. The hole array layered structure according to claim 5, wherein the first tooth slot outer contour is in a shape of a regular polygon, and the first hole contour is in a shape of a circle.

7. The hole array layered structure according to claim 5, wherein the first tooth slot outer contour is in a shape of a circle, and the first hole contour is in a non-circular shape.

8. The hole array layered structure according to claim 4, wherein, in each hole unit, on the plane perpendicular to the thickness direction of the base plate, a contour constrained by projections of the openings of the second tooth slots and extension lines thereof is the second hole contour, the second hole contour is located within the first hole contour, and the second hole contour is in a shape of a circle, the center of the first tooth slot outer contour coincides with a center of the second hole contour.

9. The hole array layered structure according to claim 8, wherein, in each hole unit, on the plane perpendicular to the thickness direction of the base plate, axes of the second tooth slots extend and intersect at the center of the second hole contour.

10. The hole array layered structure according to claim 9, wherein channels are further provided between adjacent hole units of the plurality of hole units, the channels extend in the thickness direction of the base plate, and on the plane perpendicular to the thickness direction of the base plate, projections of the channels are consistent with projections of the first tooth slot outer contours of the plurality of hole units.

11. The hole array layered structure according to claim 10, wherein side walls of the channels are provided with a plurality of third tooth slots extending outward perpendicularly to the thickness direction of the base plate.

12. The hole array layered structure according to claim 11, wherein, in each hole unit, on the plane perpendicular to the thickness direction of the base plate, axes of the plurality of third tooth slots extend and intersect at the center of the first tooth slot outer contour.

13. The hole array layered structure according to claim 4, wherein, in the hole array layered structure, the first tooth slots of one of the plurality of hole units are aligned with the first tooth slots of adjacent hole units of the plurality of hole units.

14. The hole array layered structure according to claim 4, wherein, in the hole array layered structure, the first tooth slots of one of the plurality of hole units are staggered with the first tooth slots of adjacent hole units of the plurality of hole units.

15. A biochip device, comprising:

a substrate; and the hole array layered structure according to claim 1, wherein the hole array layered structure is located on the substrate, and the first holes of the plurality of hole units are located on a side of the second holes of the plurality of hole units facing away from the substrate.

16. A precoating method for a biochip device, the method comprising the following steps:

providing the biochip device according to claim 15;

precoating the biochip device, wherein the precoating comprises any of the following processes:

(1) an evaporation-condensation process, comprising: orienting the openings of the plurality of hole units in the biochip device towards an evaporation position; providing a precoating means which contains a precoating material and placing the precoating means at the evaporation position with an opening of the precoating means facing the biochip device; heating the precoating means to an evaporation threshold; and stopping the precoating after heating for a predetermined time; and (2) a spraying process, comprising: taking the biochip device and a printer; disposing the precoating material in the printer; aligning printing heads of the printer with edges of the plurality of hole units on the biochip device; starting the printer, and spraying a predetermined amount of the precoating material into the plurality of hole units.

17. A precoating method for a biochip device, the method comprising the following steps:

providing the biochip device according to claim 15;

providing a leaking plate with leaking holes, and covering the biochip device on a side of the openings of the plurality of hole units by the leaking plate so that edges of the plurality of hole units correspond to at least one leaking hole on the leaking plate;

providing a scraping means so that an edge of the scraping means is attached to a side of the leaking plate facing away from the biochip device and the scraping means is movable relative to the leaking plate; and taking a precoating material and placing it at the scraping means, moving the scraping means to push the precoating material to move on the leaking plate, wherein when a movement track of the precoating material passes across the leaking holes, the precoating material enters the plurality of hole units through the leaking holes.

18. A precoating method for a biochip device, the method comprising the following steps:

providing the biochip device according to claim 15;

providing a printing plate which is provided with a transfer portion, wherein when the printing plate covers the biochip device on a side of the openings of the plurality of hole units, a portion of the printing plate attached to the biochip device is located within the transfer portion;

taking a precoating material and uniformly disposing the precoating material on the transfer portion; and performing a transfer printing comprising:

covering the biochip device on the side of the openings of the plurality of hole units by the printing plate provided with the precoating material on the transfer portion, transferring the precoating material from the transfer portion of the printing plate into the plurality of hole units of the biochip device, and maintaining the covering until the precoating material in the plurality of hole units reaches a precoating threshold.

19. A membrane forming method, comprising:

providing the biochip device according to claim 15;

arranging a first non-polar medium in the biochip device and forming a precoating membrane layer on a surface of the biochip device;

flowing a first polar medium through the biochip device to replace at least part of the first non-polar medium;

flowing a second non-polar medium through the biochip device to replace at least part of the first polar medium, wherein the second non-polar medium contains amphiphilic molecular materials; and flowing a second polar medium through the biochip device to replace at least part of the second non-polar medium, and forming the membrane layer at an interface between the first polar medium and the second polar medium, wherein the membrane layer contains the amphiphilic molecular materials.

20. The membrane forming method according to claim 19, wherein, before flowing the second polar medium through the biochip device, the method further comprises flowing air through the biochip device to replace at least part of the second non-polar medium.

21. A sequencing device, comprising a biochip device and a membrane layer formed by the biochip device, wherein the biochip device comprises: a substrate; and a hole array layered structure for forming a membrane forming space with the substrate, wherein the membrane forming space is adapted to form the membrane layer, and the hole array layered structure comprises:

a base plate; and a plurality of hole units provided in the base plate and arranged in an array, each hole unit penetrating through the base plate and comprising a first hole and a second hole stacked in a thickness direction of the base plate, the second hole being configured to be connected with the substrate, a projection of the first hole on a plane perpendicular to the thickness direction of the base plate having a first hole contour, a projection of the second hole on the plane perpendicular to the thickness direction of the base plate having a second hole contour, and the first hole contour surrounding the second hole contour on an outer side thereof, the second holes of the plurality of hole units are disconnected with each other to prevent mediums in the respective second holes from flowing among the second holes, and the first holes of the plurality of hole units are disconnected with each other to prevent mediums in the respective first holes from flowing among the first holes, wherein the hole array layered structure is located on the substrate, and the first holes of the plurality of hole units are located on a side of the second holes of the plurality of hole units facing away from the substrate;

each hole unit of the hole array layered structure further comprises first tooth slots extending outward from a side wall of the first hole perpendicularly to the thickness direction of the base plate, the first tooth slots are provided in a circumferential direction of the first hole, and each of the first tooth slots has an opening communicated with the first hole at the first hole contour, and in a projection on the plane perpendicular to the thickness direction of the base plate, extension lengths from slot bottoms to the openings of the respective first tooth slots are different.

* * * * *